United States Patent
Hulse et al.

(10) Patent No.: US 9,410,024 B2
(45) Date of Patent: Aug. 9, 2016

(54) AZEOTROPE-LIKE COMPOSITIONS COMPRISING 1-CHLORO-3,3,3-TRIFLUOROPROPENE

(71) Applicants: Ryan Hulse, Getzville, NY (US); Rajiv R. Singh, Getzville, NY (US); Hang T. Pham, Amherst, NY (US)

(72) Inventors: Ryan Hulse, Getzville, NY (US); Rajiv R. Singh, Getzville, NY (US); Hang T. Pham, Amherst, NY (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 0 days.

(21) Appl. No.: 14/287,705

(22) Filed: May 27, 2014

(65) Prior Publication Data
US 2014/0264148 A1 Sep. 18, 2014

Related U.S. Application Data

(62) Division of application No. 13/296,664, filed on Nov. 15, 2011, now Pat. No. 8,734,671.

(60) Provisional application No. 61/415,670, filed on Nov. 19, 2010.

(51) Int. Cl.
| | | |
|---|---|---|
| *C09K 5/04* | (2006.01) | |
| *C08J 9/14* | (2006.01) | |
| *A01N 25/06* | (2006.01) | |
| *C09K 3/30* | (2006.01) | |
| *C10M 171/00* | (2006.01) | |
| *A61Q 5/00* | (2006.01) | |
| *A61K 8/69* | (2006.01) | |
| *A61Q 13/00* | (2006.01) | |
| *A61Q 15/00* | (2006.01) | |
| *A61K 8/04* | (2006.01) | |
| *C11D 7/50* | (2006.01) | |
| *C09K 3/00* | (2006.01) | |
| *B32B 5/18* | (2006.01) | |
| *A61K 9/12* | (2006.01) | |
| *A61K 9/70* | (2006.01) | |

(52) U.S. Cl.
CPC ............... *C08J 9/144* (2013.01); *A01N 25/06* (2013.01); *A61K 8/046* (2013.01); *A61K 8/69* (2013.01); *A61K 9/124* (2013.01); *A61Q 5/00* (2013.01); *A61Q 13/00* (2013.01); *A61Q 15/00* (2013.01); *B32B 5/18* (2013.01); *C08J 9/146* (2013.01); *C08J 9/149* (2013.01); *C09K 3/00* (2013.01); *C09K 3/30* (2013.01); *C09K 5/045* (2013.01); *C10M 171/008* (2013.01); *C11D 7/5054* (2013.01); *A61K 9/122* (2013.01); *A61K 9/7015* (2013.01); *A61K 2800/5922* (2013.01); *C08J 2203/162* (2013.01); *C08J 2203/182* (2013.01); *C08J 2375/04* (2013.01); *C09K 2205/122* (2013.01); *C09K 2205/126* (2013.01); *C09K 2205/32* (2013.01); *C10M 2203/1006* (2013.01); *C10M 2205/0285* (2013.01); *C10M 2205/223* (2013.01); *C10M 2207/2805* (2013.01); *C10M 2209/1033* (2013.01); *C10N 2220/302* (2013.01); *C10N 2240/30* (2013.01); *Y10T 428/249954* (2015.04)

(58) Field of Classification Search
CPC ............ C08J 9/144; C09K 3/30; C09K 5/044
USPC .......................................................... 252/68
See application file for complete search history.

(56) References Cited

U.S. PATENT DOCUMENTS

| | | | |
|---|---|---|---|
| 2009/0253820 A1* | 10/2009 | Bowman et al. ............. | 521/170 |
| 2009/0305876 A1* | 12/2009 | Singh et al. .................. | 502/150 |
| 2010/0056657 A1* | 3/2010 | Chen et al. ..................... | 521/98 |

*Primary Examiner* — John Hardee
(74) *Attorney, Agent, or Firm* — Colleen D. Szuch

(57) ABSTRACT

An azeotrope-like mixture consisting essentially of a binary azeotrope-like mixture consisting essentially of trans-1-chloro-3,3,3-trifluoropropene (trans-HFO-1233zd) and a second component selected from the group consisting of 2,3,3-tetrafluoropropene (HFO-1234yf) and trans-1,3,3,3-tetrafluoropropene (trans-HFO-1234ze), and combinations of these and various uses thereof.

21 Claims, 1 Drawing Sheet

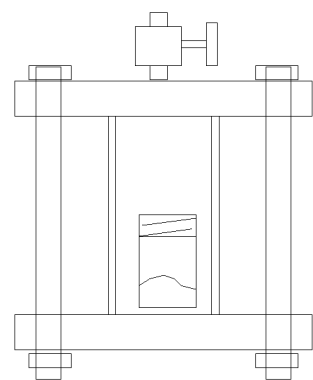

AZEOTROPE-LIKE COMPOSITIONS COMPRISING 1-CHLORO-3,3,3-TRIFLUOROPROPENE

CROSS REFERENCES TO RELATED APPLICATIONS

This application is a divisional filing of U.S. application Ser. No. 13/296,664, filed Nov. 15, 2011, now U.S. Pat. No. 8,734,671, which is related to and claims the priority benefit of U.S. provisional application No. 61/415,670 filed Nov. 19, 2010, the contents each of which are incorporated herein by reference.

FIELD OF THE INVENTION

The present invention relates generally to compositions comprising 1-chloro-3,3,3-trifluoropropene. More specifically, the present invention provides azeotrope-like compositions comprising 1-chloro-3,3,3-trifluoropropene and uses thereof.

BACKGROUND OF THE INVENTION

Fluorocarbon based fluids, including chlorofluorocarbons ("CFCs"), hydrochlorofluorocarbons ("HCFCs"), and hydrofluoroolefins ("HFOs"), have properties that are desirable in industrial refrigerants, blowing agents, heat transfer media, solvents, gaseous dielectrics, and other applications. For these applications, the use of single component fluids or azeotrope-like mixtures, i.e., those which do not substantially fractionate on boiling and evaporation, are particularly desirable. It is also considered important in many applications, including with respect to heat transfer fluids, blowing agents, propellants, solvents and aerosols, that any potential substitute also preferably possess those properties present in many of the most widely used fluids, such as excellent functional properties (for example, heat transfer properties in the case of heat transfer compositions), chemical stability, low- or no-toxicity, low- or no-flammability and/or lubricant compatibility, among others.

Unfortunately, suspected environmental problems, such as global warming and ozone depletion, and other potential problems such as a flammability level that is higher than desired, have been attributed to the use of some of these fluids, thereby limiting their contemporary use. Hydrofluoroolefins ("HFOs") have been proposed as possible replacements for such CFCs, HCFCs, and HFCs. However, the identification of new, environmentally-safe, non-fractionating mixtures comprising HFOs are complicated due to the fact that azeotrope formation is not readily predictable. Therefore, industry is continually seeking new HFO-based mixtures that are acceptable and environmentally safer substitutes for CFCs, HCFCs, HFCs and certain HFOs and mixtures of these.

This invention satisfies one or more of the above-noted or other needs.

SUMMARY OF INVENTION

Applicants have discovered azeotrope and azeotrope-like compositions comprising, preferably consisting essentially of, and even more preferably consisting of 1-chloro-3,3,3-trifluoropropene ("1233zd"), and even more preferably trans-1-chloro-3,3,3-trifluoropropene ("trans-HFO-1233zd or 1233zd(E)") and a second component selected from the group consisting of 2,3,3,3-tetrafluoropropene (HFO-1234yf) and trans-1,3,3,3-tetrafluoropropene (trans-HFO-1234ze). Preferred azeotrope and azeotrope-like mixtures of the invention exhibit characteristics which make them particularly desirable for number of applications, including as refrigerants, as blowing agents in the manufacture of insulating foams, and as solvents in a number of cleaning and other applications, as propellants, as aerosols, and as the propellant and/or the material being sprayed in other sprayable compositions. With respect to refrigeration, the present compositions are particularly useful in mobile air conditioning, including specifically automobile air conditioning, chillers, stationary refrigeration and the like.

According to one aspect of the invention, applicants have recognized that these compositions tend to exhibit relatively low global warming potentials ("GWPs"), preferably less than about 1000, more preferably less than about 500, more preferably less than about 150, and even more preferably less than about 75.

One aspect of the present invention involves a composition comprising (a) a binary azeotrope-like mixture consisting essentially of 1-chloro-3,3,3-trifluoropropene and a second component selected from selected from the group consisting of 2,3,3,3-tetrafluoropropene (HFO-1234yf) and trans-1,3,3,3-tetrafluoropropene (trans-HFO-1234ze); and (b) at least one or more adjuvant selected from: co-blowing agent, co-solvent, active ingredient, material to be sprayed, and additive such as lubricants, stabilizers, metal passivators, corrosion inhibitors, and flammability suppressants.

Another aspect of the invention provides a solvent for use in vapor degreasing, cold cleaning, wiping and similar solvent applications comprising an azeotrope-like mixture as described herein. According to another aspect of the invention, the present compositions are useful in connection with the refrigeration systems, compositions and methods wherein the composition is used as a refrigerant with enhanced oil return properties and/or as an oil return agent to enhance solubility of another refrigerant in the lubricating oil used in the refrigeration system/method. According to one embodiment of this aspect of the invention, the lubricant which is used in the refrigerant system preferably comprises, and in certain embodiments consists essentially of, polyalkylene glycol lubricant. The present compositions also have advantage in connection with refrigerant systems that include a lubricant which comprises mineral oil, either alone or together with other lubricating components.

Another aspect of the invention provides a sprayable composition comprising an azeotrope-like mixture as described herein, an active ingredient and/or material to be sprayed or applied, and, optionally, inert ingredients and/or solvents and/or other aerosol propellants.

Yet another aspect of the invention provides closed cell foam comprising a polyurethane-, polyisocyanurate-, or phenolic-based cell wall and a cell gas disposed within at least a portion of the cell wall structure, wherein the cell gas comprises the azeotrope-like mixture as described herein.

According to another embodiment, provided is a polyol premix comprising the azeotrope-like mixture described herein.

According to another embodiment, provided is a foamable composition comprising the azeotrope-like mixture described herein.

According to another embodiment, provided is a method for producing thermoset foam comprising (a) adding a blowing agent comprising an azeotrope-like composition according to claim 1 to a foamable mixture comprising a thermosetting resin; (b) reacting said foamable mixture to produce a thermoset foam; and (c) volatilizing said azeotrope-like composition during said reacting.

According to another embodiment, provided is a method for producing thermoplastic foam comprising (a) adding a blowing agent comprising an azeotrope-like composition according to claim 1 to a foamable mixture comprising a thermoplastic resin; (b) reacting said foamable mixture to produce a thermoplastic foam; and (c) volatilizing said azeotrope-like composition during said reacting.

According to another embodiment, provided is a thermoplastic foam having a cell wall comprising a thermoplastic polymer and a cell gas comprising an azeotrope-like mixture as described herein. Preferably, the thermoplastic foam comprises a cell gas having an azeotrope-like mixture as described herein and having a cell wall constructed of a thermoplastic polymer selected from polystyrene, polyethylene, polypropylene, polyvinyl chloride, polytheyenetereph-thalate or combinations thereof.

According to another embodiment, provided is a thermoset foam having a cell wall comprising a thermosetting polymer and a cell gas comprising an azeotrope-like mixture as described herein. Preferably, the thermoset foam comprises a cell gas having an azeotrope-like mixture as described herein and a cell wall comprising a thermoset polymer selected from polyurethane, polyisocyanurate, phenolic, epoxy, or combinations thereof.

According to another embodiment of the invention, provided is a refrigerant comprising an azeotrope-like mixture as described herein.

BRIEF DESCRIPTION OF THE FIGURES

FIG. 1 provides an illustration of the testing apparatus used for testing blowing agent functionality of the azeotropic compounds of the present invention.

DESCRIPTION OF PREFERRED
EMBODIMENTS

According to certain embodiments, the present invention provides azeotrope-like compositions comprising, preferably consisting essentially of, and even more preferably consisting of 1-chloro-3,3,3-trifluoropropene ("1233zd"), and even more preferably trans-1-chloro-3,3,3-trifluoropropene ("trans-HFO-1233zd or 1233zd(E)") and a second component selected from the group consisting of 2,3,3,3-tetrafluoropropene (HFO-1234yf) and trans-1,3,3,3-tetrafluoropropene (trans-HFO-1234ze). Thus, the present invention overcomes the aforementioned shortcomings by providing azeotrope-like compositions that are, in preferred embodiments, substantially free of CFCs, HCFCs, and HFCs and have very low global warming potentials, low ozone depletion potential, and/or no or mild flammability and which exhibit relatively constant boiling point characteristics.

As used herein, the term "mildly flammable" refers to compounds or compositions which are classified as being 2L in accordance with ASHRAE standard 34 dated 2010, incorporated herein by reference.

As used herein, the term "azeotrope-like" relates to compositions that are strictly azeotropic or that generally behave like azeotropic mixtures. An azeotropic mixture is a system of two or more components in which the liquid composition and vapor composition are equal at the stated pressure and temperature. In practice, this means that the components of an azeotropic mixture are constant-boiling or essentially constant-boiling and generally cannot be thermodynamically separated during a phase change. The vapor composition formed by boiling or evaporation of an azeotropic mixture is identical, or substantially identical, to the original liquid composition. Thus, the concentration of components in the liquid and vapor phases of azeotrope-like compositions change only minimally, if at all, as the composition boils or otherwise evaporates. In contrast, boiling or evaporating non-azeotropic mixtures changes the component concentrations in the liquid phase to a significant degree.

As used herein, the term "consisting essentially of", with respect to the components of an azeotrope-like composition, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds.

The term "effective amounts" as used herein refers to the amount of each component which, upon combination with the other component, results in the formation of an azeotrope-like composition of the present invention.

Unless otherwise specified, the term 1233zd means the cis-isomer, the trans-isomer, or some mixture thereof.

As used herein, the term cis-1233zd with respect to a component of an azeotrope-like mixture, means the amount cis-1233zd relative to all isomers of −1233zd in azeotrope-like compositions is at least about 95%, more preferably at least about 98%, even more preferably at least about 99%, even more preferably at least about 99.9%. In certain preferred embodiments, the cis-1233zd component in azeotrope-like compositions of the present invention is essentially pure cis-1233zd.

As used herein, the term trans-1233zd with respect to a component of an azeotrope-like mixture, means the amount trans-1233zd relative to all isomers of 1233zd in azeotrope-like compositions is at least about 95%, more preferably at least about 98%, even more preferably at least about 99%, even more preferably at least about 99.9%. In certain preferred embodiments, the trans-1233zd component in azeotrope-like compositions of the present invention is essentially pure trans-1233zd.

The term HFO-1234ze is used herein generically to refer to 1,1,1,3-tetrafluoropropene, independent of whether it is the cis- or trans-form. The terms "cis-HFO-1234ze" and "trans-HFO-1234ze" are used herein to describe the cis- and trans-forms of 1,3,3,3-tetrafluoropropene respectively. The term "HFO-1234ze" therefore includes within its scope cis-HFO-1234ze, trans-HFO-1234ze, and all combinations and mixtures of these.

As used herein, the term trans-HFO-1234ze with respect to a component of an azeotrope-like mixture, means the amount trans-HFO-1234ze relative to all isomers of trans-HFO-1234ze in azeotrope-like compositions is at least about 95%, more preferably at least about 98%, even more preferably at least about 99%, even more preferably at least about 99.9%. In certain preferred embodiments, the trans-HFO-1234ze component in azeotrope-like compositions of the present invention is essentially pure trans-HFO-1234ze.

As used herein, the term "ambient pressure" with respect to boiling point data means the atmospheric pressure surrounding the relevant medium. In general, ambient pressure is 14.7 psia, but could vary +/−0.5 psi.

The azeotrope-like compositions of the present invention can be produced by combining effective amounts of 1233zd with one or more other components, preferably in fluid form. Any of a wide variety of methods known in the art for combining two or more components to form a composition can be adapted for use in the present methods. For example, 1233zd and trans-HFO-1234ze can be mixed, blended, or otherwise combined by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

Fluoropropenes, such as $CF_3CCl=CH_2$, can be produced by known methods such as catalytic vapor phase fluorination of various saturated and unsaturated halogen-containing C3 compounds, including the method described in U.S. Pat. Nos. 2,889,379; 4,798,818 and 4,465,786, each of which is incorporated herein by reference.

EP 974,571, also incorporated herein by reference, discloses the preparation of 1,1,1,3-chlorotrifluoropropene by contacting 1,1,1,3,3-pentafluoropropane (HFC-245fa) in the vapor phase with a chromium based catalyst at elevated temperature, or in the liquid phase with an alcoholic solution of KOH, NaOH, Ca(OH)2 or Mg(OH)2. The end product is approximately 90% by weight of the trans isomer and 10% by weight cis. Preferably, the cis isomers are substantially separated from the trans forms so that the resultant preferred form of 1-chloro-3,3,3-trifluoropropene is more enriched in the cis isomer. Because the cis isomer has a boiling point of about 40° C. in contrast with the trans isomer boiling point of about 20° C., the two can easily be separated by any number of distillation methods known in the art. However, a preferred method is batch distillation. According to this method, a mixture of cis and trans 1-chloro-3,3,3-trifluoropropene is charged to the reboiler. The trans isomer is removed in the overhead leaving the cis isomer in the reboiler. The distillation can also be run in a continuous distillation where the trans isomer is removed in the overhead and the cis isomer is removed in the bottom. This distillation process can yield about 99.9+% pure trans-1-chloro-3,3,3-trifluoropropene and 99.9+% cis-1-chloro-3,3,3-trifluoropropene.

Trans-1233zd/Trans-HFO-1234ze Azeotrope-Like Compositions:

In a preferred embodiment, the azeotrope-like composition comprises effective amounts of trans-1233zd and trans-HFO-1234ze. More preferably, these binary azeotrope-like compositions consist essentially of about 80 to about 99.9 wt. % trans-HFO-1234ze and from about 0.1 to about 20 wt. % trans-1233zd, more preferably from about 83 to about 99.9 wt. % trans-HFO-1234ze and about 0.1 to about 17 wt. % trans-1233zd, and even more preferably from about 97 to about 99.7 wt. % trans-HFO-1234ze and from about 0.3 to about 3 wt. % trans-1233zd.

Preferably, the trans-1233zd/trans-HFO-1234ze compositions of the present invention have a boiling point of about −18.5±1° C. at ambient pressure as defined herein.

Trans-1233zd/HFO-1234yf Azeotrope-Like Compositions:

In a preferred embodiment, the azeotrope-like composition comprises effective amounts of trans-1233zd and HFO-1234yf. More preferably, these binary azeotrope-like compositions consist essentially of about 75 to about 99.9 wt. % HFO-1234yf and from about 0.1 to about 25 wt. % trans-1233zd, more preferably from about 85 to about 99.9 wt. % HFO-1234yf and about 0.1 to about 15 wt. % trans-1233zd, and even more preferably from about 90 to about 99.9 wt. % HFO-1234yf and from about 0.1 to about 10 wt. % trans-1233zd.

Preferably, the trans-1233zd/HFO-1234yf compositions of the present invention have a boiling point of about −28.5±1° C. at ambient pressure as defined herein.

The azeotrope-like compositions of the present invention may further include a variety of optional additives including, but not limited to, lubricants, stabilizers, metal passivators, corrosion inhibitors, flammability suppressants, and the like. Examples of suitable stabilizers include diene-based compounds, and/or phenol compounds, and/or epoxides selected from the group consisting of aromatic epoxides, alkyl epoxides, alkenyl epoxides, and combinations of two or more thereof. Preferably, these optional additives do not affect the basic azeotrope-like characteristic of the composition.

Heat Transfer Compositions

The compositions of the present invention are generally adaptable for use in heat transfer applications, that is, as a heating and/or cooling medium, including as evaporative cooling agents.

In connection with evaporative cooling applications, the compositions of the present invention are brought in contact, either directly or indirectly, with a body to be cooled and thereafter permitted to evaporate or boil while in such contact, with the preferred result that the boiling fluid in accordance with the present composition absorbs heat from the body to be cooled. In certain of such applications it may be preferred to utilize the compositions of the present invention, preferably in liquid form, by spraying or otherwise applying the liquid to the body to be cooled. In other evaporative cooling applications, it may be preferred to permit a liquid composition in accordance with the present intention to escape from a relatively high pressure container into a relatively lower pressure environment wherein the body to be cooled is in contact, either directly or indirectly, with the container enclosing the liquid composition of the present invention, preferably without recovering or recompressing the escaped gas. One particular application for this type of embodiment is the self cooling of a beverage, food item, novelty item or the like. Previous to the invention described herein, prior compositions, such as HFC-152a and HFC-134a were used for such applications. However, such compositions have recently been looked upon negatively in such application because of the negative environmental impact caused by release of these materials into the atmosphere. For example, the United States EPA has determined that the use of such prior chemicals in this application is unacceptable due to the high global warming nature of these chemicals and the resulting detrimental effect on the environment that may result from their use. The compositions of the present invention should have a distinct advantage in this regard due to their low global warming potential and low ozone depletion potential, as described herein. Additionally, the present compositions are expected to also find substantial utility in connection with the cooling of electrical or electronic components, either during manufacture or during accelerated lifetime testing. In a accelerated lifetime testing, the component is sequentially heated and cooled in rapid succession to simulate the use of the component. Such uses would therefore be of particular advantage in the semiconductor and computer board manufacturing industry. Another advantage of the present compositions in this regard is they are expected to exhibit as contagious electrical properties when used in connection with such applications. Another evaporative cooling application comprises methods for temporarily causing a discontinuation of the flow of fluid through a conduit. Preferably, such methods would include contacting the conduit, such as a water pipe through which water is flowing, with a liquid composition according to the present invention and allowing the liquid composition of the present invention to evaporate while in contact with the conduit so as to freeze liquid contained therein and thereby temporarily stop the flow of fluid through the conduit. Such methods have distinct advantage in connection with enabling the service or other work to be performed on such conduits, or systems connected to such conduits, at a location downstream of the location at which the present composition is applied.

Although it is contemplated that the compositions of the present invention may include the compounds of the present invention in widely ranging amounts, it is generally preferred that refrigerant compositions of the present invention comprise the present azeotrope or azeotrope-like composition in an amount that is at least about 50% by weight, more preferably at least about 70% by weight, and even more preferably at least about 90% by weight, of the refrigerant composition.

The relative amount of the hydrofluoroolefin used in accordance with the present invention is preferably selected to produce a heat transfer fluid which has the required heat transfer capacity, particularly refrigeration capacity, and preferably is at the same time non-flammable or mildly flammable. As used herein, the term non-flammable refers to a fluid which is non-flammable in all proportions in air as measured by ASTM E-681.

The compositions of the present invention may include other components for the purpose of enhancing or providing certain functionality to the composition, or in some cases to reduce the cost of the composition. For example, heat transfer compositions according to the present invention, especially those used in vapor compression systems, include in addition to the refrigerant comprising the present azeotrope or azeotrope-like composition, a lubricant, generally in amounts of from about 30 to about 50 percent by weight of the composition. Furthermore, the present compositions may also include a co-refrigerant, or compatibilizer, such as propane, for the purpose of aiding compatibility and/or solubility of the lubricant. Such compatibilizers, including propane, butanes and pentanes, are preferably present in amounts of from about 0.5 to about 5 percent by weight of the composition. Combinations of surfactants and solubilizing agents may also be added to the present compositions to aid oil solubility, as disclosed by U.S. Pat. No. 6,516,837, the disclosure of which is incorporated by reference. Commonly used refrigeration lubricants such as Polyol Esters (POEs) and Poly Alkylene Glycols (PAGs), PAG oils, silicone oil, mineral oil, alkyl benzenes (ABs) and poly(alpha-olefin) (PAO) that are used in refrigeration machinery with hydrofluorocarbon (HFC) refrigerants may be used with the refrigerant compositions of the present invention. Commercially available mineral oils include Witco LP 250 (registered trademark) from Witco, Zerol 300 (registered trademark) from Shrieve Chemical, Sunisco 3GS from Witco, and Calumet R015 from Calumet. Commercially available alkyl benzene lubricants include Zerol 150 (registered trademark). Commercially available esters include neopentyl glycol dipelargonate, which is available as Emery 2917 (registered trademark) and Hatcol 2370 (registered trademark). Other useful esters include phosphate esters, dibasic acid esters, and fluoroesters. In some cases, hydrocarbon based oils are have sufficient solubility with the refrigerant that is comprised of an iodocarbon, the combination of the iodocarbon and the hydrocarbon oil might more stable than other types of lubricant. Such combination may therefore be advantageous. Preferred lubricants include polyalkylene glycols and esters. Polyalkylene glycols are highly preferred in certain embodiments because they are currently in use in particular applications such as mobile air-conditioning. Of course, different mixtures of different types of lubricants may be used.

The present methods, systems and compositions are thus adaptable for use in connection with a wide variety of heat transfer systems in general and refrigeration systems in particular, such as air-conditioning (including both stationary and mobile air conditioning systems), refrigeration, heat-pump systems, and the like. In certain preferred embodiments, the compositions of the present invention are used in refrigeration systems originally designed for use with an HFC refrigerant, such as, for example, HFC-134a, or an HCFC refrigerant, such as, for example, HCFC-22. The preferred compositions of the present invention tend to exhibit many of the desirable characteristics of HFC-134a and other HFC refrigerants, including a GWP that is as low, or lower than that of conventional HFC refrigerants and a capacity that is as high or higher than such refrigerants and a capacity that is substantially similar to or substantially matches, and preferably is as high as or higher than such refrigerants. In particular, applicants have recognized that certain preferred embodiments of the present compositions tend to exhibit relatively low global warming potentials ("GWPs"), preferably less than about 1000, more preferably less than about 500, and even more preferably less than about 150. In addition, the relatively constant boiling nature of certain of the present compositions, including the azeotrope-like compositions described in the co-pending patent applications incorporated herein by reference, makes them even more desirable than certain conventional HFCs, such as R-404A or combinations of HFC-32, HFC-125 and HFC-134a (the combination HFC-32:HFC-125:HFC134a in approximate 23:25:52 weight ratio is referred to as R-407C), for use as refrigerants in many applications. Heat transfer compositions of the present invention are particularly preferred as replacements for HFC-134, HFC-152a, HFC-22, R-12 and R-500.

In certain other preferred embodiments, the present compositions are used in refrigeration systems originally designed for use with a CFC-refrigerant. Preferred refrigeration compositions of the present invention may be used in refrigeration systems containing a lubricant used conventionally with CFC-refrigerants, such as mineral oils, polyalkylbenzene, polyalkylene glycol oils, and the like, or may be used with other lubricants traditionally used with HFC refrigerants. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers (including chillers using centrifugal compressors), transport refrigeration systems, commercial refrigeration systems and the like.

Many existing refrigeration systems are currently adapted for use in connection with existing refrigerants, and the compositions of the present invention are believed to be adaptable for use in many of such systems, either with or without system modification. Many applications the compositions of the present invention may provide an advantage as a replacement in smaller systems currently based on certain refrigerants, for example those requiring a small refrigerating capacity and thereby dictating a need for relatively small compressor displacements. Furthermore, in embodiments where it is desired to use a lower capacity refrigerant composition of the present invention, for reasons of efficiency for example, to replace a refrigerant of higher capacity, such embodiments of the present compositions provide a potential advantage. Thus, it is preferred in certain embodiments to use compositions of the present invention, particularly compositions comprising a substantial proportion of, and in some embodiments consisting essentially of the present compositions, as a replacement for existing refrigerants, such as: HFC-134a; CFC-12; HCFC-22; HFC-152a; combinations of pentfluoroethane (HFC-125), trifluorethane (HFC-143a) and tetrafluoroethane (HFC-134a) (the combination HFC-125:HFC-143a: HFC134a in approximate 44:52:4 weight ratio is referred to as R-404A); combinations of HFC-32, HFC-125 and HFC-134a (the combination HFC-32:HFC-125:HFC134a in approximate 23:25:52 weight ratio is referred to as R-407C); combinations of methylene fluoride (HFC-32) and pentfluoroethane (HFC-125) (the combination HFC-32:HFC-125 in approximate 50:50 weight ratio is referred to as R-410A); the combination of CFC-12 and 1,1-difluorethane (HFC-152a) (the combination CFC-12:HFC-152a in a 73.8:26.2 weight ratio is referred to R-500); and combinations of HFC-125 and HFC-143a (the combination HFC-125:HFC143a in approximate 50:50 weight ratio is referred to as R-507A). In certain embodiments it may also be beneficial to use the present compositions in connection with the replacement of refrigerants formed from the combination HFC-32:HFC-125: HFC134a in approximate 20:40:40 weight ratio, which is referred to as R-407A, or in approximate 15:15:70 weight ratio, which is referred to as R-407D. The present compositions are also believed to be suitable as replacements for the above noted compositions in other applications, such as aerosols, blowing agents and the like, as explained elsewhere herein.

In certain applications, the refrigerants of the present invention potentially permit the beneficial use of larger displacement compressors, thereby resulting in better energy efficiency than other refrigerants, such as HFC-134a. Therefore the refrigerant compositions of the present invention provide the possibility of achieving a competitive advantage on an energy basis for refrigerant replacement applications, including automotive air conditioning systems and devices, commercial refrigeration systems and devices, chillers, residential refrigerator and freezers, general air conditioning systems, heat pumps and the like.

Many existing refrigeration systems are currently adapted for use in connection with existing refrigerants, and the compositions of the present invention are believed to be adaptable for use in many of such systems, either with or without system modification. In many applications the compositions of the present invention may provide an advantage as a replacement in systems which are currently based on refrigerants having a relatively high capacity. Furthermore, in embodiments where it is desired to use a lower capacity refrigerant composition of the present invention, for reasons of cost for example, to replace a refrigerant of higher capacity, such embodiments of the present compositions provide a potential advantage. Thus, It is preferred in certain embodiments to use compositions of the present invention, particularly compositions comprising a substantial proportion of, and in some embodiments consisting essentially of, HFO-1234 (preferably any one or more of cis-HFO-1234ze, trans-HFO-1234ze, HFO-1234yf, HFO-1234yc, HFO-1234zc, HFO-1234ye(E) and HFO-1234ye (Z)) as a replacement for existing refrigerants, such as HFC-134a. In certain applications, the refrigerants of the present invention potentially permit the beneficial use of larger displacement compressors, thereby resulting in better energy efficiency than other refrigerants, such as HFC-134a. Therefore the refrigerant compositions of the present invention, particularly compositions comprising any one or more of, cis-HFO-1234ze, trans-HFO-1234ze, HFO-1234yf, HFO-1234yc, HFO-1234zc, HFO-1234ye(E) and HFO-1234ye (Z), provide the possibility of achieving a competitive advantage on an energy basis for refrigerant replacement applications.

It is contemplated that the compositions of the present are adaptable for use in chillers typically used in connection with commercial air conditioning systems. In certain of such embodiments it is preferred to include in the present one or more of the following additional compounds that may be included primarily for their impact on the heat transfer characteristics, cost and the like. The following components may thus be included in the compositions as co-heat transfer fluids (or co-refrigerants in the case of cooling operations):
Trichlorofluoromethane (CFC-11)
Dichlorodifluoromethane (CFC-12)
Difluoromethane (HFC-32)
Pentafluoroethane (HFC-125)
1,1,2,2-tetrafluoroethane (HFC-134)
1,1,1,2-Tetrafluoroethane (HFC-134a)
Difluoroethane (HFC-152a)
1,1,1,2,3,3,3-Heptafluoropropane (HFC-227ea)
1,1,1,3,3,3-hexafluoropropane (HFC-236fa)
1,1,1,3,3-pentafluoropropane (HFC-245fa)
1,1,1,3,3-pentafluorobutane (HFC-365mfc)
water
$CO_2$ Blowing Agents In another embodiment of the invention, provided are blowing agents comprising at least one azeotrope-like mixture described herein. Polymer foams are generally of two general classes: thermoplastic foams and thermoset foams.

Thermoplastic foams are produced generally via any method known in the art, including those described in Throne, *Thermoplastic Foams,* 1996, Sherwood Publishers, Hinkley, Ohio, or Klempner and Sendijarevic, Polymeric Foams and Foam Technology, $2^{nd}$ Edition 2004, Hander Gardner Publications. Inc, Cincinnati, Ohio. For example, extruded thermoplastic foams can be prepared by an extrusion process whereby a solution of blowing agent in molten polymer, formed in an extruder under pressure, is forced through an orifice onto a moving belt at ambient temperature or pressure or optionally at reduced pressure to aid in foam expansion. The blowing agent vaporizes and causes the polymer to expand. The polymer simultaneously expands and cools under conditions that give it enough strength to maintain dimensional stability at the time corresponding to maximum expansion. Polymers used for the production of extruded thermoplastic foams include, but are not limited to, polystyrene, polyethylene (HDPE, LDPE, and LLDPE), polypropylene, polyethylene terephthalate, ethylene vinyl acetate, and mixtures thereof.

According to certain preferred aspects of the present invention, the present compositions are used as blowing agent, or as part of a foamable composition, preferably wherein the foamable composition is a thermoplastic, and even more preferably a polystyrene-based formulation. Applicants have surprisingly found that the compositions of the present invention possess, in certain embodiments, enhanced solubility in the polymeric component a foamable compositions, and thus have the capability of providing foams products, and particularly closed cell foam products, with improved physical properties and characteristics, including enhanced and unexpectedly superior cell structure and/or sell distribution and/or cell size.

A number of additives are optionally added to the molten polymer solution to optimize foam processing and properties including, but not limited to, nucleating agents (e.g., talc), flame retardants, colorants, processing aids (e.g., waxes), cross linking agents, permeability modifiers, and the like. Additional processing steps such as irradiation to increase cross linking, lamination of a surface film to improve foam skin quality, trimming and planning to achieve foam dimension requirements, and other processes may also be included in the manufacturing process.

In general, the blowing agent may include the azeotrope-like compositions of the present invention in widely ranging amounts. It is generally preferred, however, that the blowing agents comprise at least about 15% by weight of the blowing agent. In certain preferred embodiments, the blowing agent comprises at least about 50% by weight of the present compositions, and in certain embodiments the blowing agent consists essentially of the present azeotrope-like composition. In certain preferred embodiments, the blowing agent includes, in addition to the present azeotrope-like mixtures, one or more co-blowing agents, fillers, vapor pressure modifiers, flame suppressants, stabilizers, and like adjuvants.

In certain preferred embodiments, the blowing agent is characterized as a physical (i.e., volatile) blowing agent comprising the azeotrope-like mixture of the present invention. In general, the amount of blowing agent present in the blended mixture is dictated by the desired foam densities of the final foams products and by the pressure and solubility limits of the process. For example, the proportions of blowing agent in parts by weight can fall within the range of about 1 to about 45 parts, more preferably from about 4 to about 30 parts, of blowing agent per 100 parts by weight of polymer. The blowing agent may comprise additional components mixed with the azeotrope-like composition, including chlorofluorocarbons such as trichlorofluoromethane (CFC-11), dichlorodifluoromethane (CFC-12), hydrochlorofluorocarbons such as 1,1-dichloro-1-fluoroethane (HCFC-141b), 1-chloro-1,1-difluoroethane (HCFC-142b), chlorodifluoromethane (HCFC-22), hydrofluorocarbons such as 1,1,1,2-tetrafluoroethane (HFC-134a), 1,1-difluoroethane (HFC-152a), 1,1,1,3,3-pentafluoropropane (HFC-245fa), and 1,1,1,3,3-pentafluorobutane (HFC-365mfc), hydrocarbons such as propane, butane, isobutane, cyclopentane, carbon dioxide, chlorinated hydrocarbons alcohols, ethers, ketones and mixtures thereof.

In certain embodiments, the blowing agent is characterized as a chemical blowing agent. Chemical blowing agents are materials that, when exposed to temperature and pressure conditions in the extruder, decompose to liberate a gas, generally carbon dioxide, carbon monoxide, nitrogen, hydrogen, ammonia, nitrous oxide, of mixtures thereof. The amount of chemical blowing agent present is dependent on the desired final foam density. The proportions in parts by weight of the total chemical blowing agent blend can fall within the range of from less than 1 to about 15 parts, preferably from about 1 to about 10 parts, of blowing agent per 100 parts by weight of polymer.

In certain preferred embodiments, dispersing agents, cell stabilizers, surfactants and other additives may also be incorporated into the blowing agent compositions of the present invention. Surfactants are optional, but preferably are added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which are incorporated herein by reference. Other optional additives for the blowing agent mixture include flame retardants or suppressants such as tri(2-chloroethyl)phosphate, tri(2-chloropropyl)phosphate, tri(2,3-dibromopropyl)-phosphate, tri(1,3-dichloropropyl)phosphate, diammonium phosphate, various halogenated aromatic compounds, antimony oxide, aluminum trihydrate, polyvinyl chloride, and the like.

With respect to thermoset foams, in general any thermoset polymer can be used, including but not limited to polyurethane, polyisocyanurate, phenolic, epoxy, and combinations thereof. In general these foams are produced by bringing together chemically reactive components in the presence of one or more blowing agents, including the azeotrope-like composition of this invention and optionally other additives, including but not limited to cell stabilizers, solubility enhancers, catalysts, flame retardants, auxiliary blowing agents, inert fillers, dyes, and the like.

With respect to the preparation of polyurethane or polyisocyanurate foams using the azeotrope like compositions described in the invention, any of the methods well known in the art can be employed, see Saunders and Frisch, *Volumes I and II Polyurethanes Chemistry and Technology* (1962) John Wiley and Sons, New York, N.Y. In general, polyurethane or polyisocyanurate foams are prepared by combining an isocyanate, a polyol or mixture of polyols, a blowing agent or mixture of blowing agents, and other materials such as catalysts, surfactants, and optionally, flame retardants, colorants, or other additives.

It is convenient in many applications to provide the components for polyurethane or polyisocyanurate foams in preblended formulations. Most typically, the foam formulation is preblended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, water, and even other polyols can be added as a third stream to the mix head or reaction site. Most conveniently, however, they are all incorporated into one B Component as described above.

Any organic polyisocyanate can be employed in polyurethane or polyisocyanurate foam synthesis inclusive of aliphatic and aromatic polyisocyanates. Preferred as a class are the aromatic polyisocyanates. Typical aliphatic polyisocyanates are alkylene diisocyanates such as tri, tetra, and hexamethylene diisocyanate, isophorene diisocyanate, 4,4'-methylenebis(cyclohexyl isocyanate), and the like; typical aromatic polyisocyanates include m-, and p-phenylene diisocyanate, polymethylene polyphenyl isocyanate, 2,4- and 2,6-toluenediisocyanate, dianisidine diisocyanate, bitoylene isocyanate, naphthylene 1,4-diisocyanate, bis(4-isocyanatophenyl)methene, bis(2-methyl-4-isocyanatophenyl)methane, and the like.

Preferred polyisocyanates are the polymethylene polyphenyl isocyanates, particularly the mixtures containing from about 30 to about 85 percent by weight of methylenebis (phenyl isocyanate) with the remainder of the mixture comprising the polymethylene polyphenyl polyisocyanates of functionality higher than 2.

Typical polyols used in the manufacture of polyurethane foams include, but are not limited to, aromatic amino-based polyether polyols such as those based on mixtures of 2,4- and 2,6-toluenediamine condensed with ethylene oxide and/or propylene oxide. These polyols find utility in pour-in-place molded foams. Another example is aromatic alkylamino-based polyether polyols such as those based on ethoxylated and/or propoxylated aminoethylated nonylphenol derivatives. These polyols generally find utility in spray applied polyurethane foams. Another example is sucrose-based polyols such as those based on sucrose derivatives and/or mixtures of sucrose and glycerine derivatives condensed with ethylene oxide and/or propylene oxide.

Examples of polyols used in polyurethane modified polyisocyanurate foams include, but are not limited to, aromatic polyester polyols such as those based on complex mixtures of phthalate-type or terephthalate-type esters formed from polyols such as ethylene glycol, diethylene glycol, or propylene glycol. These polyols are used in rigid laminated boardstock, can be blended with other types of polyols such as sucrose based polyols, and used in other polyurethane foam applications such as described above.

Catalysts used in the manufacture of polyurethane foams are typically tertiary amines including, but not limited to, N-alkylmorpholines, N-alkylalkanolamines, N,N-dialkylcyclohexylamines, and alkylamines where the alkyl groups are methyl, ethyl, propyl, butyl, and the like and isomeric forms thereof; and hetrocyclic amines. Typical, but not limiting examples are triethylenediamine, tetramethylethylenediamine, bis(2-dimethylaminoethyl)ether, triethylamine, tripropylamine, tributylamine, triamylamine, pyridine, quinoline, dimethylpiperazine, piperazine, N,N-dimethylcyclohexylamine, N-ethylmorpholine, 2-methylpiperazine, N,N-dimethylethanolamine, tetramethylpropanediamine, methyltriethylenediamine, and the like, and mixtures thereof.

Optionally, non-amine polyurethane catalysts are used. Typical of such catalysts are organometallic compounds of bismuth, lead, tin, titanium, antimony, uranium, cadmium, cobalt, thorium, aluminum, mercury, zinc, nickel, cerium, molybdenum, vanadium, copper, manganese, zirconium, and the like. Included as illustrative are bismuth nitrate, lead 2-ethylhexoate, lead benzoate, ferric chloride, antimony trichloride and antimony glycolate. A preferred organo-tin class includes the stannous salts of carboxylic acids such as stannous octoate, stannous 2-ethylhexoate, stannous laurate, and the like, as well as dialkyl tin salts of carboxylic acids such as dibutyl tin diacetate, dibutyl tin dilaurate, dioctyl tin diacetate, and the like.

In the preparation of polyisocyanurate foams, trimerization catalysts are used for the purpose of converting the blends in conjunction with excess A component to polyisocyanurate-polyurethane foams. The trimerization catalysts employed can be any catalyst known to one skilled in the art, including, but not limited to, glycine salts and tertiary amine trimerization catalysts and alkali metal carboxylic acid salts and mixtures of the various types of catalysts. Preferred species within the classes are potassium acetate, potassium octoate, and N-(2-hydroxy-5-nonylphenol)methyl-N-methylglycinate.

Dispersing agents, cell stabilizers, and surfactants can be incorporated into the present blends. Surfactants, which are, generally, polysiloxane polyoxyalkylene block co-polymers, such as those disclosed in U.S. Pat. Nos. 2,834,748, 2,917,480, and 2,846,458, which are incorporated herein by reference.

Other optional additives for the blends can include flame retardants such as tris(2-chloroethyl)phosphate, tris(2-chloropropyl)phosphate, tris(2,3-dibromopropyl)phosphate, tris (1,3-dichloropropyl)phosphate, diammonium phosphate, various halogenated aromatic compounds, antimony oxide, aluminum trihydrate, polyvinyl chloride, and the like. Other optional ingredients can include from 0 to about 3 percent water, which chemically reacts with the isocyanate to produce carbon dioxide. This carbon dioxide acts as an auxiliary blowing agent.

Also included in the mixture are blowing agents or blowing agent blends as disclosed in this invention. Generally speaking, the amount of blowing agent present in the blended mixture is dictated by the desired foam densities of the final polyurethane or polyisocyanurate foams product. The proportions in parts by weight of the total blowing agent blend can fall within the range of from 1 to about 45 parts of blowing agent per 100 parts of polyol, preferably from about 4 to about 30 parts.

The polyurethane foams produced can vary in density from about 0.5 pound per cubic foot to about 40 pounds per cubic foot, preferably from about 1.0 to 20.0 pounds per cubic foot, and most preferably from about 1.5 to 6.0 pounds per cubic foot. The density obtained is a function of how much of the blowing agent or blowing agent mixture disclosed in this invention is present in the A and/or B components, or alternatively added at the time the foam is prepared.

Foams and Foamable Compositions

Certain embodiments of the present invention involve a foam comprising a polyurethane-, polyisocyanurate-, or phenolic-based cell wall and a cell gas disposed within at least a portion of the cells, wherein the cell gas comprises the azeotrope-like mixture described herein. In certain embodiments, the foams are extruded thermoplastic foams. Preferred foams have a density ranging from about 0.5 pounds per cubic foot to about 60 pounds per cubic foot, preferably from about 1.0 to 20.0 pounds per cubic foot, and most preferably from about 1.5 to 6.0 pounds per cubic foot. The foam density is a function of how much of the blowing agent or blowing agent mixture (i.e., the azeotrope-like mixture and any auxiliary blowing agent, such as carbon dioxide, chemical blowing agent or other co-blowing agent) is present in the molten polymer. These foams are generally rigid but can be made in various grades of softness to suit the end use requirements. The foams can have a closed cell structure, an open cell structure or a mixture of open and closed cells, with closed cell structures being preferred. These foams are used in a variety of well known applications, including but not limited to thermal insulation, flotation, packaging, void filling, crafts and decorative, and shock absorption.

In other embodiments, the invention provides foamable compositions. The foamable compositions of the present invention generally include one or more components capable of forming foam, such as polyurethane, polyisocyanurate, and phenolic-based compositions, and a blowing agent comprising at least one azeotrope-like mixture described herein. In certain embodiments, the foamable composition comprises thermoplastic materials, particularly thermoplastic polymers and/or resins. Examples of thermoplastic foam components include polyolefins, such as polystyrene (PS), polyethylene (PE), polypropylene (PP) and polyethyleneterepthalate (PET), and foams formed therefrom, preferably low-density foams. In certain embodiments, the thermoplastic foamable composition is an extrudable composition.

In certain embodiments, provided is a method for producing such foams. It will be appreciated by those skilled in the art, especially in view of the disclosure contained herein, that the order and manner in which the blowing agent is formed and/or added to the foamable composition does not generally affect the operability of the present invention. For example, in the case of extrudable foams, it is possible to mix in advance the various components of the blowing agent. In certain embodiments, the components of the foamable composition are not mixed in advance of introduction to the extrusion equipment or are not added to the same location in the extrusion equipment. Thus, in certain embodiments it may be desired to introduce one or more components of the blowing agent at first location in the extruder, which is upstream of the place of addition of one or more other components of the blowing agent, with the expectation that the components will come together in the extruder and/or operate more effectively in this manner. In certain other embodiments, two or more components of the blowing agent are combined in advance and introduced together into the foamable composition, either directly or as part of premix which is then further added to other parts of the foamable composition.

Solvent/Sprayable Compositions

In a preferred embodiment, the azeotrope-like compositions of this invention may be used as solvents and/or as the propellant in sprayable compositions, either alone or in combination with other known propellants and/or solvents. The solvent composition comprises, more preferably consists essentially of, and, even more preferably, consists of the azeotrope-like compositions of the invention. In certain embodiments, the sprayable composition is an aerosol.

In certain preferred embodiments, provided is a sprayable composition comprising a solvent as described above, an active ingredient, and optionally, other components such as inert ingredients, solvents, and the like.

In another aspect, the present invention provides propellant compositions comprising or consisting essentially of a composition of the present invention. In certain preferred embodiments, such propellant composition is preferably a sprayable composition Suitable active materials to be sprayed include, without limitation, cosmetic materials such as deodorants, perfumes, hair sprays, cleaning solvents, lubricants, insecticides as well as medicinal materials, such as anti-asthma medications. The term medicinal materials is used herein in its broadest sense to include any and all materials which are, or at least are believe to be, effective in connection with therapeutic, diagnostic, pain relief, and similar treatments, and as such would include for example drugs and biologically active substances.

In one aspect, the present compositions may be used for propelling objects, including solid and/or liquid objects and/or gaseous objects, by applying to such objects a force generated by the present composition, such as would occur through the expansion of the compositions of the present invention. For example, such force may preferably be provided, at least in part, by the change of phase of the compositions of the present invention from liquid to gas, and/or by the force released as a result of a substantial pressure reduction as the composition of the present invention exits from a pressurized container. In this way, the compositions of the present invention may be used to apply a burst of force, or a sustained force to an object to be propelled. Accordingly, the present invention comprises systems, containers and devices which include compositions of the present invention and which are configured to propel or move an object, either a liquid object or a solid object or a gaseous object, with the desired amount of force. Examples of such uses include containers (such as pressurized cans and similar devices) which may be used, through the propellant force, to unblock drains, pipes or blockages in conduits, channels or nozzles. Another application includes use of the present composition to propel solid objects through the environment, particularly the ambient air, such as bullets, pellets, grenades, nets, canisters, bean bags, electrodes or other individual tethered or untethered projectiles. In other embodiments, the present compositions may be used to impart motion, such as a spitting motion, to gyroscopes, centrifuges, toys or other bodies to be rotated, or to impart a propelling force to solid objects, such as fireworks, confetti, pellets, munitions and other solid objects. In other applications, the force provided by the compositions of the present invention may be used to push or steer bodies in motion, including rockets or other projectiles.

The propellant compositions of the present invention preferably comprise a material to be sprayed and a propellant comprising, consisting essentially of, or consisting of a composition in accordance with the present invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleaning solvents, and lubricants, as well as medicinal materials such as anti-asthma medications. The term medicinal materials is used herein in its broadest sense to include any and all materials which are, or at least are believe to be, effective in connection with therapeutic treatments, diagnostic methods, pain relief, and similar treatments, and as such would include for example drugs and biologically active substances. The medicinal material in certain preferred embodiments are adapted to be inhaled. The medicament or other therapeutic agent is preferably present in the composition in a therapeutic amount, with a substantial portion of the balance of the composition comprising a an azeotrope or azeotrope-like composition of the present invention.

Aerosol products for industrial, consumer or medical use typically contain one or more propellants along with one or more active ingredients, inert ingredients or solvents. The propellant provides the force that expels the product in aerosolized form. While some aerosol products are propelled with compressed gases like carbon dioxide, nitrogen, nitrous oxide and even air, most commercial aerosols use liquefied gas propellants. The most commonly used liquefied gas propellants are hydrocarbons such as butane, isobutane, and propane. Dimethyl ether and HFC-152a (1,1-difluoroethane) are also used, either alone or in blends with the hydrocarbon propellants. Unfortunately, all of these liquefied gas propellants are highly flammable and their incorporation into aerosol formulations will often result in flammable aerosol products.

Applicants have come to appreciate the continuing need for nonflammable, liquefied gas propellants with which to formulate aerosol products. The present invention provides compositions of the present invention for use in certain industrial aerosol products, including for example spray cleaners, lubricants, and the like, and in medicinal aerosols, including for example to deliver medications to the lungs or mucosal membranes. Examples of this includes metered dose inhalers (MDIs) for the treatment of asthma and other chronic obstructive pulmonary diseases and for delivery of medicaments to accessible mucous membranes or intranasally. The present invention thus includes methods for treating ailments, diseases and similar health related problems of an organism (such as a human or animal) comprising applying a composition of the present invention containing a medicament or other therapeutic component to the organism in need of treatment. In certain preferred embodiments, the step of applying the present composition comprises providing a MDI containing the composition of the present invention (for example, introducing the composition into the MDI) and then discharging the present composition from the MDI.

The compositions of the present invention are capable of providing nonflammable, liquefied gas propellant and aerosols that do not contribute substantially to global warming. The present compositions can be used to formulate a variety of industrial aerosols or other sprayable compositions such as contact cleaners, dusters, lubricant sprays, and the like, and consumer aerosols such as personal care products, household products and automotive products. HFO-1234ze is particularly preferred for use as an important component of propellant compositions for in medicinal aerosols such as metered dose inhalers. The medicinal aerosol and/or propellant and/or sprayable compositions of the present invention in many applications include, in addition to azeotrope or azeotrope-like composition of the present invention, a medicament such as a beta-agonist, a corticosteroid or other medicament, and, optionally, other ingredients, such as surfactants, solvents, other propellants, flavorants and other excipients. The compositions of the present invention, unlike many compositions previously used in these applications, have good environmental properties and are not considered to be potential contributors to global warming. The present compositions therefore provide in certain preferred embodiments substantially nonflammable, liquefied gas propellants having very low Global Warming potentials.

Flavorants and Fragrances

The compositions of the present invention also provide advantage when used as part of, and in particular as a carrier for, flavor formulations and fragrance formulations. The suitability of the present compositions for this purpose is demonstrated by a test procedure in which 0.39 grams of Jasmone were put into a heavy walled glass tube. 1.73 grams of an azeotrope composition of the present invention comprising in one case trans-HFO-1234ze and HFO-1234yf in another case were added to the glass tube. The tube was then frozen and sealed. Upon thawing the tube, it was found that the mixture had one liquid phase. The solution contained 20 wt. % Jasome and 80 wt. % of the azeotrope composition of the present inventions, thus establishing favorable use a carrier for flavor formulations and fragrances. It also establishes its potential as an extractant of biologically active compounds (such as Biomass) and fragrances, including from plant matter. In certain embodiments, it may be preferred to use the present composition for in extraction applications with the present fluid in its supercritical state. This an other applications of involving use of the present compositions in the supercritical or near supercritical state are described hereinafter.

Inflating Agents

One potential advantage of the compositions of the present invention is that the preferred compositions are in a gaseous state under most ambient conditions. This characteristic allows them to fill the space while not adding significantly to the weight of the space being spilled. Furthermore, the compositions of the present invention are able to be compressed or liquefied for relatively easy transportation and storage. Thus, for example, the compositions of the present invention may be included, preferably but not necessarily in liquid form, in a closed container, such as a pressurized can, which has a nozzle therein adapted to release the composition into another environment in which it will exist, at least for a period of time, as a pressurized gas. For example, such an application may include including the present compositions in a can adapted to connect to tires such as may be used on transportation vehicles (including cars, trucks and aircraft). Other examples in accordance with this embodiment include the use of the present compositions, in a similar arrangement, to inflate air bags or other bladders (including other protective bladders) adapted to contain, at least for a period of time, a gaseous material under pressure. Alternatively to the use of a fixed container, such as I can, the present compositions may be applied in accordance with this aspect of the invention through a hose or other system that contains the present composition, either in liquid or gaseous form, and through which it can be introduced into such a pressurized environment as is required for the particular application.

Solvents and Cleaning Compositions

In another embodiment of the invention, the azeotrope-like compositions described herein can be used as a solvent in cleaning various soils such as mineral oil, rosin based fluxes, silicon oils, lubricants, etc., from various substrates by wiping, vapor degreasing, or other means. In certain preferred embodiments, the cleaning composition is an aerosol.

Methods and Systems

The compositions of the present invention are useful in connection with numerous methods and systems, including as heat transfer fluids in methods and systems for transferring heat, such as refrigerants used in refrigeration, air conditioning and heat pump systems. The present compositions are also advantageous for in use in systems and methods of generating aerosols, preferably comprising or consisting of the aerosol propellant in such systems and methods. Methods of forming foams and methods of extinguishing and suppressing fire are also included in certain aspects of the present invention. The present invention also provides in certain aspects methods of removing residue from articles in which the present compositions are used as solvent compositions in such methods and systems.

Heat Transfer Methods and Systems

The preferred heat transfer methods generally comprise providing a composition of the present invention and causing heat to be transferred to or from the composition, either by sensible heat transfer, phase change heat transfer, or a combination of these. For example, in certain preferred embodiments the present methods provide refrigeration systems comprising a refrigerant of the present invention and methods of producing heating or cooling by condensing and/or evaporating a composition of the present invention. In certain preferred embodiments, the methods for cooling, including cooling of other fluid either directly or indirectly or a body directly or indirectly, comprise condensing a refrigerant composition comprising a composition of the present invention and thereafter evaporating said refrigerant composition in the vicinity of the article to be cooled. As used herein, the term "body" is intended to refer not only to inanimate objects but also to living tissue, including animal tissue in general and human tissue in particular. For example, certain aspects of the present invention involve application of the present composition to human tissue for one or more therapeutic purposes, such as a pain killing technique, as a preparatory anesthetic, or as part of a therapy involving reducing the temperature of the body being treated. In certain embodiments, the application to the body comprises providing the present compositions in liquid form under pressure, preferably in a pressurized container having a one-way discharge valve and/or nozzle, and releasing the liquid from the pressurized container by spraying or otherwise applying the composition to the body. As the liquid evaporates from the surface being sprayed, the surface cools.

Certain preferred methods for heating a fluid or body comprise condensing a refrigerant composition comprising a composition of the present invention in the vicinity of the fluid or body to be heated and thereafter evaporating said refrigerant composition. In light of the disclosure herein, those of skill in the art will be readily able to heat and cool articles according to the present inventions without undue experimentation.

Applicants have found that in the systems and methods of the present invention many of the important refrigeration system performance parameters are relatively close to the parameters for R-134a. Since many existing refrigeration systems have been designed for R-134a, or for other refrigerants with properties similar to R-134a, those skilled in the art will appreciate the substantial advantage of a low GWP and/or a low ozone depleting refrigerant that can be used as replacement for R-134a or like refrigerants with relatively minimal modifications to the system. It is contemplated that in certain embodiments the present invention provides retrofitting methods which comprise replacing the heat transfer fluid (such as a refrigerant) in an existing system with a composition of the present invention, without substantial modification of the system. In certain preferred embodiments the replacement step is a drop-in replacement in the sense that no substantial redesign of the system is required and no major item of equipment needs to be replaced in order to accommodate the composition of the present invention as the heat transfer fluid. In certain preferred embodiments, the methods comprise a drop-in replacement in which the capacity of the system is at least about 70%, preferably at least about 85%, and even more preferably at least about 90% of the system capacity prior to replacement. In certain preferred embodiments, the methods comprise a drop-in replacement in which the suction pressure and/or the discharge pressure of the system, and even more preferably both, is/are at least about 70%, more preferably at least about 90% and even more preferably at least about 95% of the suction pressure and/or the discharge pressure prior to replacement. In certain preferred embodiments, the methods comprise a drop-in replacement in which the mass flow of the system is at least about 80%, and even more preferably at least 90% of the mass flow prior to replacement.

In certain embodiments the present invention provides cooling by absorbing heat from a fluid or body, preferably by evaporating the present refrigerant composition in the vicinity of the body or fluid to be cooled to produce vapor comprising the present composition. Preferably the methods include the further step of compressing the refrigerant vapor, usually with a compressor or similar equipment to produce vapor of the present composition at a relatively elevated pressure. Generally, the step of compressing the vapor results in the addition of heat to the vapor, thus causing an increase in the temperature of the relatively high pressure vapor. Preferably in such embodiments the present methods include removing from this relatively high temperature, high pressure vapor at least a portion of the heat added by the evaporation and compression steps. The heat removal step preferably includes condensing the high temperature, high pressure vapor while the vapor is in a relatively high pressure condition to produce a relatively high pressure liquid comprising a composition of the present invention. This relatively high pressure liquid preferably then undergoes a nominally isoenthalpic reduction in pressure to produce a relatively low temperature, low pressure liquid. In such embodiments, it is this reduced temperature refrigerant liquid which is then vaporized by heat transferred from the body or fluid to be cooled.

In another process embodiment of the invention, the compositions of the invention may be used in a method for producing heating which comprises condensing a refrigerant comprising the compositions in the vicinity of a liquid or body to be heated. Such methods, as mentioned hereinbefore, frequently are reverse cycles to the refrigeration cycle described above.

Cleaning Methods

The present invention also provides methods of removing containments from a product, part, component, substrate, or any other article or portion thereof by applying to the article a composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material.

Preferred methods of the present invention comprise applying the present composition to the article. Although it is contemplated that numerous and varied cleaning techniques can employ the compositions of the present invention to good advantage, it is considered to be particularly advantageous to use the present compositions in connection with supercritical cleaning techniques. Supercritical cleaning is disclosed in U.S. Pat. No. 6,589,355, which is assigned to the assignee of the present invention and incorporated herein by reference. For supercritical cleaning applications, is preferred in certain embodiments to include in the present cleaning compositions, in addition to the azeotrope or azeotrope-like compositions, one or more additional components, such as CO2 and other additional components known for use in connection with supercritical cleaning applications. It may also be possible and desirable in certain embodiments to use the present cleaning compositions in connection with particular vapor degreasing and solvent cleaning methods.

Flammability Reduction Methods

According to certain other preferred embodiments, the present invention provides methods for reducing the flammability of fluids, said methods comprising adding a compound or composition of the present invention to said fluid. The flammability associated with any of a wide range of otherwise flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of the present compounds or compositions may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of compound or composition added to the flammable fluid is effective to render the resulting fluid substantially non-flammable.

Flame Suppression Methods

The present invention further provides methods of suppressing a flame, said methods comprising contacting a flame with a fluid comprising a compound or composition of the present invention. Any suitable methods for contacting the flame with the present composition may be used. For example, a composition of the present invention may be sprayed, poured, and the like onto the flame, or at least a portion of the flame may be immersed in the composition. In light of the teachings herein, those of skill in the art will be readily able to adapt a variety of conventional apparatus and methods of flame suppression for use in the present invention.

Sterilization Methods

Many articles, devices and materials, particularly for use in the medical field, must be sterilized prior to use for the health and safety reasons, such as the health and safety of patients and hospital staff. The present invention provides methods of sterilizing comprising contacting the articles, devices or material to be sterilized with a composition of the present invention comprising, in addition to the azeotrope or azeotrope-like compositions, one or more costerilizing agents. While many sterilizing agents are known in the art and are considered to be adaptable for use in connection with the present invention, in certain preferred embodiments sterilizing agent comprises ethylene oxide, formaldehyde, hydrogen peroxide, chlorine dioxide, ozone and combinations of these. In certain embodiments, ethylene oxide is the preferred sterilizing agent. Those skilled in the art, in view of the teachings contained herein, will be able to readily determine the relative proportions of sterilizing agent and the present compound(s) to be used in connection with the present sterilizing compositions and methods, and all such ranges are within the broad scope hereof. As is known to those skilled in the art, certain sterilizing agents, such as ethylene oxide, are relatively flammable components, and the compound(s) in accordance with the present invention are included in the present compositions in amounts effective, together with other components present in the composition, to reduce the flammability of the sterilizing composition to acceptable levels.

The sterilization methods of the present invention may be either high or low-temperature sterilization of the present invention involves the use of a compound or composition of the present invention at a temperature of from about 250° F. to about 270° F., preferably in a substantially sealed chamber. The process can be completed usually in less than about 2 hours. However, some articles, such as plastic articles and electrical components, cannot withstand such high temperatures and require low-temperature sterilization. In low temperature sterilization methods, the article to be sterilized is exposed to a fluid comprising a composition of the present invention at a temperature of from about room temperature to about 200° F., more preferably at a temperature of from about room temperature to about 100° F.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber. Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

EXAMPLES

The invention is further illustrated in the following example which is intended to be illustrative, but not limiting in any manner. For the relevant examples, an ebulliometer of the general type described by Swietolslowski in his book "Ebulliometric Measurements" (Reinhold, 1945) was used.

Example 1

An ebulliometer consisting of vacuum jacketed tube with a condenser on top which is further equipped with a Quartz Thermometer is used. About 20.58 g of 1234yf was initially charged into the ebulliometer. Then 1233zd(E) was added in small, measured increments. A temperature depression is observed at 14.4 psia when 1233zd(E) is added to 1234yf, indicating that a binary minimum boiling azeotrope is formed. From greater than about 0 to about 20 weight percent 1233zd(E), the boiling point of the mixture stays below the boiling point of 1234yf.

TABLE 1

| T(C.) | Wt. % HFO-1234yf | Wt. % 1233zd(E) |
|---|---|---|
| −28.7 | 100.0 | 0.0 |
| −28.9 | 99.7 | 0.3 |
| −29.0 | 99.1 | 0.9 |
| −29.1 | 97.9 | 2.1 |
| −29.2 | 96.8 | 3.2 |
| −29.2 | 95.1 | 4.9 |
| −29.1 | 93.4 | 6.6 |
| −28.9 | 89.4 | 10.6 |
| −28.7 | 85.6 | 14.4 |
| −28.5 | 82.2 | 17.8 |
| −28.2 | 78.3 | 21.7 |

Example 2

An ebulliometer consisting of vacuum jacketed tube with a condenser on top which is further equipped with a Quartz Thermometer is used. About 20.3 g of 1234ze(E) was initially charged into the ebulliometer. Then 1233zd(E) was added in small, measured increments. A temperature depression is observed at 14.4 psia when 1233zd(E) is added to 1234ze(E), indicating that a binary minimum boiling azeotrope is formed. From greater than about 0 to about 3.3 weight percent 1233zd(E), the boiling point of the mixture stays below the boiling point of 1234yf.

TABLE 2

| T(° C.) | Wt. % 1234ze(E) | Wt. % 1233zd(E) |
|---|---|---|
| −19.0 | 100.0 | 0.0 |
| −19.1 | 99.7 | 0.3 |
| −19.2 | 99.1 | 0.9 |
| −19.1 | 97.9 | 2.1 |
| −19.0 | 96.7 | 3.3 |
| −18.8 | 93.4 | 6.6 |
| −18.5 | 90.3 | 9.7 |
| −18.3 | 87.4 | 12.6 |
| −18.0 | 82.9 | 17.1 |

Example 3

An azeotrope-like mixture containing 98% by weight HFO-1234yf and about 2% by weight trans-1233zd is loaded into an aerosol can. An aerosol valve is crimped into place and HFC-134a is added through the valve to achieve a pressure in the can of about 20 psig. The mixture is then sprayed onto surface demonstrating that the azeotropic mixture is useful as an aerosol. The aerosol is used effectively to spray at least one active ingredient selected from the group consisting of deodorants, perfumes, hair sprays, cleaning solvents, lubricants, insecticides, and medicinal materials.

Example 4

An azeotrope-like mixture containing 90% by weight HFO-1234yf and about 10% by weight trans-1233zd is loaded into an aerosol can. An aerosol valve is crimped into place and HFC-134a is added through the valve to achieve a pressure in the can of about 20 psig. The mixture is then sprayed onto surface demonstrating that the azeotropic mixture is useful as an aerosol. The aerosol is used effectively to spray at least one active ingredient selected from the group consisting of deodorants, perfumes, hair sprays, cleaning solvents, lubricants, insecticides, and medicinal materials.

Example 5

An azeotrope-like mixture containing 80% by weight HFO-1234yf and about 20% by weight trans-1233zd is loaded into an aerosol can. An aerosol valve is crimped into place and if needed HFC-134a is added through the valve to achieve a pressure in the can of about 20 psig. The mixture is then sprayed onto surface demonstrating that the azeotropic mixture is useful as an aerosol. The aerosol is used effectively to spray at least one active ingredient selected from the group consisting of deodorants, perfumes, hair sprays, cleaning solvents, lubricants, insecticides, and medicinal materials.

Example 6

An azeotrope-like mixture containing 98% by weight trans-HFO-1234ze and about 2% by weight trans-1233zd is loaded into an aerosol can. An aerosol valve is crimped into place and if needed HFC-134a is added through the valve to achieve a pressure in the can of about 20 psig. The mixture is then sprayed onto surface demonstrating that the azeotropic mixture is useful as an aerosol. The aerosol is used effectively to spray at least one active ingredient selected from the group consisting of deodorants, perfumes, hair sprays, cleaning solvents, lubricants, insecticides, and medicinal materials.

Example 7

An azeotrope-like mixture containing 95% by weight trans-HFO-1234ze and about 5% by weight trans-1233zd is loaded into an aerosol can. An aerosol valve is crimped into place and if needed HFC-134a is added through the valve to achieve a pressure in the can of about 20 psig. The mixture is then sprayed onto surface demonstrating that the azeotropic mixture is useful as an aerosol. The aerosol is used effectively to spray at least one active ingredient selected from the group consisting of deodorants, perfumes, hair sprays, cleaning solvents, lubricants, insecticides, and medicinal materials.

Example 8

An azeotrope-like mixture containing 85% by weight trans-HFO-1234ze and about 15% by weight trans-1233zd is loaded into an aerosol can. An aerosol valve is crimped into place and if needed HFC-134a is added through the valve to achieve a pressure in the can of about 20 psig. The mixture is then sprayed onto surface demonstrating that the azeotropic mixture is useful as an aerosol. The aerosol is used effectively to spray at least one active ingredient selected from the group consisting of deodorants, perfumes, hair sprays, cleaning solvents, lubricants, insecticides, and medicinal materials.

Example 9

The coefficient of performance (COP) is a universally accepted measure of refrigerant performance, especially useful in representing the relative thermodynamic efficiency of a refrigerant in a specific heating or cooling cycle involving evaporation or condensation of the refrigerant. In refrigeration engineering, this term expresses the ratio of useful refrigeration to the energy applied by the compressor in compressing the vapor. The capacity of a refrigerant represents the amount of cooling or heating it provides and provides some measure of the capability of a compressor to pump quantities of heat for a given volumetric flow rate of refrigerant. In other words, given a specific compressor, a refrigerant with a higher capacity will deliver more cooling or heating power. One means for estimating COP of a refrigerant at specific operating conditions is from the thermodynamic properties of the refrigerant using standard refrigeration cycle analysis techniques (see for example, R. C. Downing, FLUOROCARBON REFRIGERANTS HANDBOOK, Chapter 3, Prentice-Hall, 1988).

A refrigeration/air conditioning cycle system is provided where the condenser temperature is about 150° F. and the evaporator temperature is about −35° F. under nominally isentropic compression with a compressor inlet temperature of about 50° F. COP is determined for several compositions of the present invention over a range of condenser and evaporator temperatures and reported in Table 3 below, based upon HFC-134a having a COP value of 1.00, a capacity value of 1.00 and a discharge temperature of 175° F.

TABLE 3

| AZEOTROPE-LIKE REFRIGERANT COMPOSITION | Approximate Relative COP | Approximate Relative CAPACITY | Approximate DISCHARGE TEMPERATURE (° F.) |
|---|---|---|---|
| trans-HFO-1234ze/trans-1233zd | 0.8-1.2 | 0.7-1.3 | 160-170 |
| HFO 1234yf/trans-1233zd | 0.8-1.21 | 0.7-1.3 | 160-170 |

This example shows that the azeotrope-like compositions of the present invention each have an energy efficiency about equal to or better than HFC-134a and the compressor using the present refrigerant compositions will produce discharge temperatures which are advantageous. In certain preferred embodiments, therefore, the present invention provides methods for heating or cooling an article or fluid comprising using a composition of the present invention in which the capacity of the refrigeration system is at least about 100%, more preferably at least about 105% of the capacity of the same system with R-134a used as the refrigerant.

Example 10

The miscibility of the azeotrope-like compositions of the present invention with various refrigeration lubricants is tested. The lubricants tested are mineral oil (C3), alkyl benzene (Zerol 150), ester oil (Mobil EAL 22 cc and Solest 120), polyalkylene glycol (PAG) oil (Goodwrench Refrigeration Oil for 134a systems), and a poly(alpha-olefin) oil (CP-6005-100). For each refrigerant/oil combination, three compositions are tested, namely 5, 20 and 50 weight percent of lubricant, with the balance of each being the azeotrope-like compositions of the present invention being tested The lubricant compositions are placed in heavy-walled glass tubes. The tubes are evacuated, the refrigerant compound in accordance with the present invention is added, and the tubes are then sealed. The tubes are then put into an air bath environmental chamber, the temperature of which is varied from about −50° C. to 70° C. At roughly 10° C. intervals, visual observations of the tube contents are made for the existence of one or more liquid phases. In a case where more than one liquid phase is observed, the mixture is reported to be immiscible. In a case where there is only one liquid phase observed, the mixture is reported to be miscible. In those cases where two liquid phases were observed, but with one of the liquid phases occupying only a very small volume, the mixture is reported to be partially miscible.

The polyalkylene glycol and ester oil lubricants are miscible in all tested proportions over the entire temperature range.

Example 11

The compatibility of the refrigerant the azeotrope-like compositions of the present invention with PAG lubricating oils while in contact with metals used in refrigeration and air conditioning systems is tested at 350° C., representing conditions much more severe than are found in many refrigeration and air conditioning applications.

Aluminum, copper and steel coupons are added to heavy walled glass tubes. Two grams of oil are added to the tubes. The tubes are then evacuated and one gram of refrigerant is added. The tubes are put into an oven at 350° F. for one week and visual observations are made. At the end of the exposure period, the tubes are removed.

This procedure was done for the following combinations of oil and the azeotrope-like compositions of the present invention:
trans-1233zd/trans-HFO-1234ze and GM Goodwrench PAG oil
trans-1233zd/trans-HFO-1234ze and GM Goodwrench oil PAG oil
trans-1233zd/trans-HFO-1234ze and MOPAR-56 PAG oil
trans-1233zd/trans-HFO-1234ze and MOPAR-56 PAG oil
trans-1233zd/trans-HFO-1234ze and MOPAR-56 PAG oil.
trans-1233zd/trans-HFO-1234ze and GM Goodwrench PAG oil
tran-1233zd/HFO-1234yf and GM Goodwrench oil PAG oil
trans-1233zd/HFO-1234yf and MOPAR-56 PAG oil
trans-1233zd/HFO-1234yf and MOPAR-56 PAG oil
trans-1233zd/HFO-1234yf and MOPAR-56 PAG oil.

In all cases, there is minimal change in the appearance of the contents of the tube. This indicates that the compositions of the present invention are stable in contact with aluminum, steel and copper found in refrigeration and air conditioning systems, and the types of lubricating oils that are likely to be included in such compositions or used with such compositions in these types of systems Example 12

This example illustrates the performance of the azeotrope and azeotrope-like compositions of the present invention being used as a working fluid in a refrigerant system, High Temperature Heat Pump and Organic Rankine Cycle system. An example of the first system is one having an Evaporation Temperature of about of 35° F. and a Condensing Temperature of about 150° F. For the purposes of convenience, such heat transfer systems, that is, systems having an evaporator temperature of from about 35° F. to about 50° F. and a CT of from about 80° F. to about 120° F., are referred to herein as "chiller" or "chiller AC" systems. The operation of each of such systems using R-123 for the purposes of comparison and a refrigeration composition of the present invention is reported in Table 4 below:

TABLE 4

| | Chiller Temp Conditions 40° F. ET and 95° F. CT | | | |
|---|---|---|---|---|
| Performance Property | Units | R-123 | Azeotrope of trans-1233zd and trans-HFO-1234ze | Azeotrope of trans-1233zd and HFO-1234yf |
| Approx. Capacity | | | | |
| Rel to R-123 | % | 100 | 110-130% | 100-110% |
| Approx. COP | | | | |
| Rel to R-123 | % | 100 | 90-110% | 100-110% |

As can be seen from the Table above, many of the important refrigeration system performance parameters are relatively close to the parameters for R-123. Since many existing refrigeration systems have been designed for R-123, or for other refrigerants with properties similar to R-123, those skilled in the art will appreciate the substantial advantage of a low GWP and/or a low ozone depleting refrigerant that can be used as replacement for R-123 or like high boiling refrigerants with relatively minimal modifications to the system. It is contemplated that in certain embodiments the present invention provides retrofitting methods which comprise replacing the refrigerant in an existing system with a composition of the present invention, preferably without substantial modification of the design.

Example 13

This example illustrates the performance of one embodiment of the present invention in which a refrigerant composition comprising the azeotrope or azeotrope-like composition of the present invention used as a heat transfer fluid in a refrigerant system, High Temperature Heat Pump or an Organic Rankine Cycle system. An example of the first system is one having an Evaporation Temperature of about of 35° F. and a Condensing Temperature of about 150° F. For the purposes of convenience, such heat transfer systems, that is, systems having an evaporator temperature of from about 35° F. to about 50° F. and a CT of from about 80° F. to about 120° F., are referred to herein as "chiller" or "chiller AC" systems The operation of each of such systems using R-123 and a refrigeration composition comprising an azeotrope or azeotrope-like composition of the present invention is reported in Table 5 below:

TABLE 5

Chiller Temp Conditions 40° F. ET and 95° F. CT

| Performance Property | Units | R-123 | Azeotrope of trans-1233zd and trans-HFO-1234ze | Azeotrope of trans-1233zd and HFO-1234yf |
|---|---|---|---|---|
| Approx. Capacity | | | | |
| Rel to R-123 | % | 100 | 110-120% | 90-100% |
| Approx. COP | | | | |
| Rel to R-123 | % | 100 | 90-110% | 100-110% |

As can be seen from the Table above, many of the important refrigeration system performance parameters are relatively close to the parameters for R-123. Since many existing refrigeration systems have been designed for R-123, or for other refrigerants with properties similar to R-123, those skilled in the art will appreciate the substantial advantage of a low GWP and/or a low ozone depleting refrigerant that can be used as replacement for R-123 or like high boiling refrigerants with relatively minimal modifications to the system. It is contemplated that in certain embodiments the present invention provided retrofitting methods which comprise replacing the refrigerant in an existing system with a composition of the present invention, preferably without substantial modification of the design.

Example 14

This example illustrates the performance of one embodiment of the present invention in which a refrigerant composition comprising the azeotrope or azeotrope-like composition of the present invention is used as a replacement for HFC-134a in four refrigerant systems. The first system is one have an evaporator temperature (ET) of about 20° F. and condenser temperature (CT) of about 130° F. (Example 54A). For the purposes of convenience, such heat transfer systems, that is, systems having an ET of from about 0 to about 35 and a CT of from about 80° F. to about 130° F., are referred to herein as "medium temperature" systems. The second system is one have an ET of about −10° F. and a CT of about 110° F. (Example 54B). For the purposes of convenience, such heat transfer systems, that is, systems having an evaporator temperature of from about −20° F. to about 20° F. and a CT of from about 80° F. to about 130° F., are referred to herein as "refrig/freezer" systems. The third system is one have an ET of about of 35° F. and a CT of about 150° F. (Example 154). For the purposes of convenience, such heat transfer systems, that is, systems having an evaporator temperature of from about 30° F. to about 60° F. and a CT of from about 90° F. to about 200° F., are referred to herein as "automotive AC" systems. The fourth system is one have an ET of about 40° F. and a CT of about 60° F. (Example 54D). For the purposes of convenience, such heat transfer systems, that is, systems having an evaporator temperature of from about 35° F. to about 50° F. and a CT of from about 80° F. to about 120° F., are referred to herein as "chiller" or "chiller AC" systems The operation of each of such systems using R-134a and a refrigeration composition comprising an azeotrope or azeotrope-like composition based on HFO-1234yf is reported in Tables 6A-D below:

TABLE 6A

Medium Temp Conditions 20° F. ET and 130° F. CT

| Performance Property | Units | R-134a | Azeotrope of trans-1233zd and HFO-1234yf |
|---|---|---|---|
| Capacity* | Btu/hr | 2541 | 2500-2550 |
| Rel to R-134a | % | | 95-1051% |
| COP | | 2.31 | 2-2.5 |
| Rel to R-134a | % | | 95-105% |
| Discharge Press. | Psig | 198.7 | 180-200 |
| Rel to R-134a | % | | 90-100% |
| Suction Press. | Psig | 18.4 | 20-25 |
| Rel to R-134a | % | | 110-125% |
| Mass Flow | Lb/hr | 0.673 | 0.958 |
| Rel to R-134a | % | | 130-150% |

*Capacity per CFM of compressor displacement (Volumetric Capacity)

TABLE 6B

Refrig/Freezer Temp Conditions 10° F. ET and 110° F. CT

| Performance Property | Units | R-134a | Azeotrope of trans-1233zd and HFO-1234yf |
|---|---|---|---|
| Capacity* | Btu/hr | 1234 | 1280-1300 |
| Rel to R-134a | % | | 100-110% |
| COP | | 1.77 | 1.5-2.0 |
| Rel to R-134a | % | | 90-100% |
| Discharge Press. | psig | 146.4 | 140-150 |
| Rel to R-134a | % | | 95-105% |
| Suction Press. | psig | 1.9 | 5-7 |
| Rel to R-134a | % | | 275-350% |
| Mass Flow | lb/hr | 0.342 | 0.4-0.45 |
| Rel to R-134a | % | | 115-130% |

*Capacity per CFM of compressor displacement (Volumetric Capacity)

TABLE 6C

Auto AC Temp Conditions 35° F. ET and 150° F. CT

| Performance Property | Units | R-134a | Azeotrope of trans-1233zd and HFO-1234yf |
|---|---|---|---|
| Capacity* | Btu/hr | 2754 | 2600-2630 |
| Rel to R-134a | % | | 90-100% |
| COP | | 1.91 | 1.8-1.9 |
| Rel to R-134a | % | | 90-100% |
| Discharge Press. | psig | 262.9 | 250-250 |
| Rel to R-134a | % | | 90-100% |

TABLE 6C-continued

Auto AC Temp Conditions 35° F. ET and 150° F. CT

| Performance Property | Units | R-134a | Azeotrope of trans-1233zd and HFO-1234yf |
|---|---|---|---|
| Suction Press. | psig | 30.4 | 34-35 |
| Rel to R-134a | % |  | 110-115% |
| Mass Flow | lb/hr | 0.891 | 1.2-1.3 |
| Rel to R-134a | % |  | 130-140% |

*Capacity per CFM of compressor displacement (Volumetric Capacity)

TABLE 6D

Chiller Temp Conditions 40° F. ET and 95° F. CT

| Performance Property | Units | R-134a | Azeotrope of trans-1233zd and HFO-1234yf |
|---|---|---|---|
| Capacity* | Btu/hr | 4236 | 4000-4100 |
| Rel to R-134a | % |  | 90-100% |
| COP | — | 6.34 | 6.2-6.3 |
| Rel to R-134a | % |  | 95-100% |
| Discharge Press. | psig | 113.9 | 113-1145 |
| Rel to R-134a | % |  | 95-100% |
| Suction Press. | psig | 35.0 | 35-40 |
| Rel to R-134a | % |  | 105-115% |
| Mass Flow | lb/hr | 1.034 | 1.2-1.3 |
| Rel to R-134a | % |  | 120-130% |

*Capacity per CFM of compressor displacement (Volumetric Capacity)

As can be seen from the Tables above, many of the important refrigeration system performance parameters are relatively close to the parameters for R-134a. Since many existing refrigeration systems have been designed for R-134a, or for other refrigerants with properties similar to R-134a, those skilled in the art will appreciate the substantial advantage of a low GWP and/or a low ozone depleting refrigerant that can be used as replacement for R-134a or like refrigerants with relatively minimal modifications to the system. It is contemplated that in certain embodiments the present invention provided retrofitting methods which comprise replacing the refrigerant in an existing system with a composition of the present invention, without substantial modification of the system. In certain preferred embodiments the replacement step is a drop-in replacement in the sense that no substantial redesign of the system is required and no major item of equipment needs to be replaced in order to accommodate the refrigerant of the present invention.

Example 15

Polyol Foam

This example illustrates the use of blowing agent in accordance with one of the preferred embodiments of the present invention, namely the use of an azeotrope or azeotrope-like composition based on trans-HFO-1234ze, and the production of polyol foams in accordance with the present invention. The components of a polyol foam formulation are prepared in accordance with the following Table 7:

TABLE 7

|  | PBW |
|---|---|
| Polyol Component |  |
| Voranol 490 | 50 |
| Voranol 391 | 50 |

TABLE 7-continued

|  | PBW |
|---|---|
| Water | 0.5 |
| B-8462 (surfactant) | 2.0 |
| Polycat 8 | 0.3 |
| Polycat 41 | 3.0 |
| trans-1233zd/ trans-HFO-1234ze | 35 |
| Total | 140.8 |
| Isocyanate |  |
| M-20S | 123.8 Index 1.10 |

*Voranol 490 is a sucrose-based polyol and Voranol 391 is a toluene diamine based polyol, and each are from Dow Chemical. B-8462 is a surfactant available from Degussa-Goldschmidt. Polycat catalysts are tertiary amine based and are available from Air Products. Isocyanate M-20S is a product of Bayer LLC.

The foam is prepared by first mixing the ingredients thereof, but without the addition of blowing agent. Two Fisher-Porter tubes are each filled with about 52.6 grams of the polyol mixture (without blowing agent) and sealed and placed in a refrigerator to cool and form a slight vacuum. Using gas burets, about 17.4 grams of the azeotrope are added to each tube, and the tubes are then placed in an ultrasound bath in warm water and allowed to sit for 30 minutes. The solution produced is hazy, and a vapor pressure measurement at room temperature indicates a vapor pressure of about 70 psig indicating that the blowing agent is not in solution. The tubes are then placed in a freezer at 27° F. for 2 hours. The vapor pressure was again measured and found to be about 14-psig. The isocyanate mixture, about 87.9 grams, is placed into a metal container and placed in a refrigerator and allowed to cool to about 50° F. The polyol tubes were then opened and weighed into a metal mixing container (about 100 grams of polyol blend are used). The isocyanate from the cooled metal container is then immediately poured into the polyol and mixed with an air mixer with double propellers at 3000 RPM's for 10 seconds. The blend immediately begins to froth with the agitation and is then poured into an 8×8×4 inch box and allowed to foam. Because of the froth, a cream time can not be measured. The foam has about a 4-minute gel time and about a 5-minute tack free time. The foam is then allowed to cure for two days at room temperature.

The foam is then cut to samples suitable for measuring physical properties and is found to have a density of about 2 pcf. K-factors are measured and found to be as indicated in the following Table 83:

TABLE 8

| Temperature | K, BTU In/Ft$^2$ h ° F. |
|---|---|
| 40° F. | 0.14-0.16 |
| 75° F. | 0.16-2.0 |
| 110° F. | 0.16-2.0 |

Example 16

Polystyrene Foam

This example illustrates the use of blowing agent in accordance with two preferred embodiments of the present invention, namely the use of an azeotrope based on trans-HFO-1234ze and an azeotrope based on HFO-1234yf, and the production of polystyrene foam. A testing apparatus and protocol has been established as an aid to determining whether a specific blowing agent and polymer are capable of producing a foam and the quality of the foam. Ground polymer (Dow Polystyrene 685D) and blowing agent consisting essentially of trans-1233zd/trans-HFO-1234ze azeotrope and blowing agent consisting essentially of trans-1233zd/HFO-1234yf azeotrope are combined in a vessel. A sketch of the vessel is illustrated in FIG. 1. The vessel volume is 200 cm$^3$ and it is made from two pipe flanges and a section of 2-inch diameter schedule 40 stainless steel pipe 4 inches long. The vessel is placed in an oven, with temperature set at from about 190° F. to about 285° F., preferably for polystyrene at 265° F., and remains there until temperature equilibrium is reached.

The pressure in the vessel is then released, quickly producing a foamed polymer. The blowing agent plasticizes the polymer as it dissolves into it. The resulting density of the two foams thus produced using this method are given in Table 9 as the density of the foams produced using trans-HFO-1234ze and HFO-1234yf. The data show that foam polystyrene is obtainable in accordance with the present invention. The die temperature for R1234ze with polystyrene is about 250° F.

TABLE 9

| | Dow polystyrene 685D Foam density (lb/ft$^3$) | |
| --- | --- | --- |
| T ° F. | Azeotrope of trans-1233zd and trans-HFO-1234ze | Azeotrope of trans-1233zd and HFO-1234yf |
| 275 | 50-60 | |
| 260 | 20-25 | 13-18 |
| 250 | 75-80 | 22-26 |
| 240 | 15-20 | |

This example demonstrates the performance of each composition of the present invention alone as a blowing agent for polystyrene foam formed in a twin screw type extruder. The apparatus employed in this example is a Leistritz twin screw extruder having the following characteristics:
30 mm co-rotating screws
L:D Ratio=40:1
The extruder is divided into 10 sections, each representing a L:D of 4:1. The polystyrene resin was introduced into the first section, the blowing agent was introduced into the sixth section, with the extrudate exiting the tenth section. The extruder operated primarily as a melt/mixing extruder. A subsequent cooling extruder is connected in tandem, for which the design characteristics were:
Leistritz twin screw extruder
40 mm co-rotating screws
L:D Ratio=40:1
Die: 5.0 mm circular
Polystyrene resin, namely Nova Chemical—general extrusion grade polystyrene, identified as Nova 1600, is feed to the extruder under the conditions indicated above. The resin has a recommended melt temperature of 375° F.-525° F. The pressure of the extruder at the die is about 1320 pounds per square inch (psi), and the temperature at the die is about 115° C.
A blowing agent consisting essentially of each of the above-notes azeotropic compositions is added to the extruder at the location indicated above, with about 0.5% by weight of talc being included, on the basis of the total blowing agent, as a nucleating agent. Foam is produced using the blowing agent at concentrations of 10% by weight, 12% by weight, and 14% by weight, in accordance with the present invention. The density of the foam produced is in the range of about 0.1 grams per cubic centimeter to 0.05 grams per cubic centimeter, with a cell size of about 45 to about 70 microns. The foams, of approximately 30 millimeters diameter, are visually of very good quality, very fine cell size, with no visible or apparent blow holes or voids.

Example 16a

Polystyrene Foam

This procedure of Example 15 is repeated except that the foaming agent comprises about 50% by weight of each of the above-notes azeotropes and 50% by weight of HFC-245fa and nucleating agent in the concentration indicated in Example 15. Foamed polystyrene is prepared at blowing agent concentrations of approximately 10% and 12%. The density of the foam produced is about 0.1 grams per cubic centimeter, with a cell size of about 200 microns. The foams, of approximately 30 millimeters diameter, are visually of very good quality, fine cell structure, with no visible or apparent voids.

Example 16b

Polystyrene Foam

This procedure of Example 15 is repeated except that the foaming agent comprises about 80% by weight of each of the above-notes azeotropes and 20% by weight of HFC-245fa and nucleating agent in the concentration indicated in Example 15. Foamed polystyrene is prepared at blowing agent concentrations of approximately 10% and 12%. The density of the foam produced is about 0.1 grams per cubic centimeter, with a cell size of about 120 microns. The foams, of approximately 30 millimeters diameter, are visually of very good quality, fine cell structure, with no visible or apparent voids.

Example 17

Polyurethane Foam Compressive Strength

This example demonstrates the performance of a trans-HFO-1234ze based azeotrope of the present invention, used in combination with hydrocarbon co-blowing agents, and in particular cyclopentane co-blowing agents in compressive strength performance of polyurethane foams.

A commercially available, refrigeration appliance-type polyurethane foam formulation (foam forming agent) is provided. The polyol blend consisted of commercial polyol(s), catalyst(s), and surfactant(s). This formulation is adapted for use in connection with a gaseous blowing agent. Standard commercial polyurethane processing equipment is used for the foam forming process. A gaseous blowing agent combination was formed comprising trans-HFO-1234ze based azeotrope in a concentration of approximately 60 mole percent, and cyclopentane in a concentration of approximately 40 mole percent of the total blowing agent. This example illustrates the physical property performance. Table 10 below reports the compressive strength of similar machine-made polyurethane foams using a blowing agent of the present invention in comparison to foams made using a blowing agent consisting of HFC-245fa and a blowing agent consisting of cyclopentane.

TABLE 10

| | Compressive Strength | |
|---|---|---|
| | Parallel % Yield | Perpendicular % Yield |
| Blowing Agent | | |
| trans-1233zd/ HFO1234ze/cyclopentane | 13-14 | 14-15 |
| HFC-245fa | 13-14 | 14.5-15.5 |
| Cyclopentane | 11.462 | 10.559 |

Example 18

Trans-1233zd Azeotropes as Solvent

An azeotrope based on trans-HFO-1234ze and an azeotrope based on HFO-1234yf was transferred to a glass container. A silicon lubricant, particularly a high-viscosity (12,500 cP) silicone oil, was added to each azeotrope to a concentration of about 10 weight percent. This resulted in a homogeneous, single-phase solution, demonstrating that each azeotrope dissolves silicone based lubricant oils.

Example 19

Trans-1233zd Azeotropes as Cleaning Agent

A metal coupon was coated with rosin-based solder flux and allowed to dry. The coupon was weighed and then dipped in an azeotrope based on trans-HFO-1234ze and an azeotrope based on HFO-1234yf. The coupon was removed, allowed to dry and reweighed to determine how much solder flux was removed. In duplicate runs, an average of 25% by weight of the flux was removed.

Example 20

Trans-1233zd Azeotropes as Extractant

A medicament, particularly a plant-derived Artemisinin which is an anti-malarial drug, is extracted from the *Artemisia annua* plant. A sample of Artemisinin was weighed into a vial. An azeotrope based on trans-HFO-1234ze and an azeotrope based on HFO-1234yf was added to the vial until the Artemisinin dissolved. The results showed that medicaments, particularly plant-derived medicaments such as Artemisinin is soluble up to approximately 3 weight percent in each azeotrope, demonstrating that it can be used to extract the drug from biomass.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention.

Accordingly, the foregoing description is by way of example only, and not limiting. The invention is limited only as defined in the following claims and equivalents thereto.

The invention claimed is:

1. A binary azeotrope or azeotrope-like mixture consisting essentially of from 2.1 to 6.6 weight percent trans-1-chloro-3,3,3-trifluoropropene (trans-HFO-1233zd) and from 93.4 to 97.9 weight percent 2,3,3,3-tetrafluoropropene (HFO-1234yf).

2. The composition of claim 1 further comprising at least one additional component selected from lubricants, stabilizers, metal passivators, corrosion inhibitors, flammability suppressants, and combinations of these.

3. A heat transfer composition comprising a refrigerant consisting essentially of the composition of claim 1.

4. The heat transfer composition of claim 3 having a global warming potential (GWP) of less than about 1000.

5. The heat transfer composition of claim 3 having a global warming potential (GWP) of less than about 500.

6. The heat transfer composition of claim 3 having a global warming potential (GWP) of less than about 150.

7. The heat transfer composition of claim 3 having a global warming potential (GWP) of less than about 75.

8. The heat transfer composition of claim 3 classified as being 2L according to ASHRAE standard 34 dated 2010.

9. A heat transfer method comprising transferring heat by causing a phase change in the composition of claim 1.

10. The composition of claim 1 further comprising at least one additional component selected from co-blowing agent, co-solvent, active ingredient, a material to be sprayed, lubricants, stabilizers, metal passivators, corrosion inhibitors, flammability suppressants, solvents and combinations of these.

11. A solvent composition comprising the composition of claim 1.

12. A cleaning method comprising applying the solvent composition of claim 11 to a material or object to be cleaned.

13. The cleaning method of claim 12 wherein said applying step comprises spraying.

14. The cleaning method of claim 12 comprising vapor degreasing.

15. A sprayable composition comprising the composition of claim 1.

16. The sprayable composition of claim 15 in the form of an aerosol.

17. A blowing agent comprising the composition of claim 1.

18. A closed cell foam comprising a polyurethane-, polyisocyanurate-, or phenolic-based cell wall and a cell gas disposed within at least a portion of the cell wall structure, wherein the cell gas comprises the blowing agent of claim 17.

19. A polyol premix composition comprising the blowing agent of claim 17.

20. A foamable composition comprising the blowing agent of claim 17.

21. The composition of claim 1 wherein said binary azeotrope or azeotrope-like mixture is an azeotropic composition.

* * * * *